(12) United States Patent
Tai

(10) Patent No.: US 12,109,164 B2
(45) Date of Patent: Oct. 8, 2024

(54) VIBRATING MASTURBATOR DEVICE WITH STERILIZATION AND CHARGING FUNCTIONS

(71) Applicant: California Exotic Novelties LLC

(72) Inventor: Chih-Yao Tai, Dongguan (CN)

(73) Assignee: California Exotic Novelties LLC, Ontario, CA (US)

( * ) Notice: Subject to any disclaimer, the term of this patent is extended or adjusted under 35 U.S.C. 154(b) by 815 days.

(21) Appl. No.: 17/301,973

(22) Filed: Apr. 20, 2021

(65) Prior Publication Data

US 2022/0087896 A1    Mar. 24, 2022

(51) Int. Cl.
| | | |
|---|---|---|
| *A61H 19/00* | (2006.01) | |
| *A61L 2/10* | (2006.01) | |
| *H02J 7/00* | (2006.01) | |

(52) U.S. Cl.
CPC ............. *A61H 19/34* (2013.01); *A61L 2/10* (2013.01); *H02J 7/0042* (2013.01); *A61L 2202/11* (2013.01); *A61L 2202/14* (2013.01)

(58) Field of Classification Search
None
See application file for complete search history.

(56) References Cited

U.S. PATENT DOCUMENTS

| | | | |
|---|---|---|---|
| 2015/0164738 A1* | 6/2015 | Caropelo | A61H 19/30 601/46 |
| 2019/0165585 A1* | 5/2019 | Grison | B65D 55/02 |

FOREIGN PATENT DOCUMENTS

| | | | | |
|---|---|---|---|---|
| CN | 211209898 U | * | 8/2020 | |
| WO | WO-2007000013 A1 | * | 1/2007 | A61H 19/00 |

* cited by examiner

*Primary Examiner* — Thaddeus B Cox

(57) ABSTRACT

A vibrating masturbator device with sterilization and charging functions, including a masturbator device and a charging box for placing and charging the masturbator device. In an embodiment, the masturbator device includes a body, a switch control member on the body, charging contacts exposed on the body, a masturbator device battery electrically connected to the charging contacts, and a vibration motor powered by the battery. In an embodiment, the masturbator device charging box includes a storage compartment for receiving the masturbator device, charging contacts corresponding in position to the charging contacts on the masturbator device, a charging box power source electrically connected to the charging box charging contacts, and a sterilization device arranged to sterilize the masturbator device while it is being charged in the charging box, the sterilization device being powered by the charging box power source.

20 Claims, 3 Drawing Sheets

VIBRATING MASTURBATOR DEVICE WITH STERILIZATION AND CHARGING FUNCTIONS

BACKGROUND

1. Field

The present disclosure relates to the technical field of health products, and in particular to vibrating masturbator devices and the sterilization and charging thereof.

2. Description of the Prior Art

With the continuous and rapid development of society, people are pursuing both material and spiritual demands. Currently, most people have a well-off life, and enjoy the happiness brought by rich materials. When the material demands reach a peak, people will seek the spiritual demands. However, the pressure brought by working and society makes people suffer stress physically and spiritually, which makes people rarely talk with each other, and even affects the lives of husband and wife, causing disharmony between them.

At present, most females would use masturbator devices to meet their mental demands. Some existing masturbator devices are too big to be taken about, and are not disinfected after using, which could easily cause infection when they are used again. Therefore, there is a need to solve the technical problems that exist currently.

SUMMARY

The technical problems regarding the current technical disadvantages as above described are solved by a vibrating masturbator device product with sterilization and charging functions. The vibrating masturbator device product includes a vibrating masturbator device and a charging box for placing and charging the masturbator device.

In embodiment, the masturbator device includes a body, a switch control member on the body, charging contacts exposed on the body, a masturbator device battery electrically connected to the charging contacts, and a vibration motor powered by the battery.

In an embodiment, the masturbator device charging box includes a storage compartment for receiving the masturbator device, charging contacts corresponding in position to the charging contacts on the masturbator device, a charging box power source electrically connected to the charging box charging contacts, and a sterilization device arranged to sterilize the masturbator device while it is being charged in the charging box, the sterilization device being powered by the charging box power source.

In an embodiment, the masturbator device includes an outer shell, a shell and a switch control button located on an upper end of the shell. A joint between the outer shell and the shell is provided with a ring-shaped charging sheet. The shell is provided with a first magnetic device, a masturbator device battery, a vibration motor and a switch control plate. The first magnetic device is provided on both sides of the shell, and the masturbator device battery is connected electrically to the ring-shaped charging sheet.

In an embodiment, the masturbator device charging box includes a charging box housing and a storage compartment inside the charging box housing, a charging box battery, a sterilization device, a second magnetic device and a power board. The sterilization device is in a bottom of the storage compartment, and the power board includes a power indicator located at a front of the storage compartment. The second magnetic device is fixed on both sides of the storage compartment and corresponds to the position of the first magnetic device on the masturbator device. The sterilization device and the charging box battery are electrically connected with the power board.

In an embodiment, the masturbator device charging box has a flip-open lid, and an upper inner end of the charging box has a protective gasket.

In an embodiment, the sterilization device in the masturbator device charging box is composed of multiple UVC ultraviolet disinfection lamps.

In an embodiment, the storage compartment in the masturbator device charging box has charging contacts corresponding to the position of the ring-shaped charging sheet on the masturbator device.

In an embodiment, the first magnetic device in the masturbator device and the second magnetic device in the charging box are mutually attracted.

In an embodiment, the masturbator device charging box has a charging port for charging the battery in the charging box.

In an embodiment, the outer shell of the masturbator device is connected and fixed with the shell of the masturbator device by a fastener.

BRIEF DESCRIPTION OF THE DRAWINGS

The foregoing and other features and advantages will be apparent from the following more particular description of example embodiments, as illustrated in the accompanying Drawings.

DETAILED DESCRIPTION OF EXAMPLE EMBODIMENTS

Figure 1:
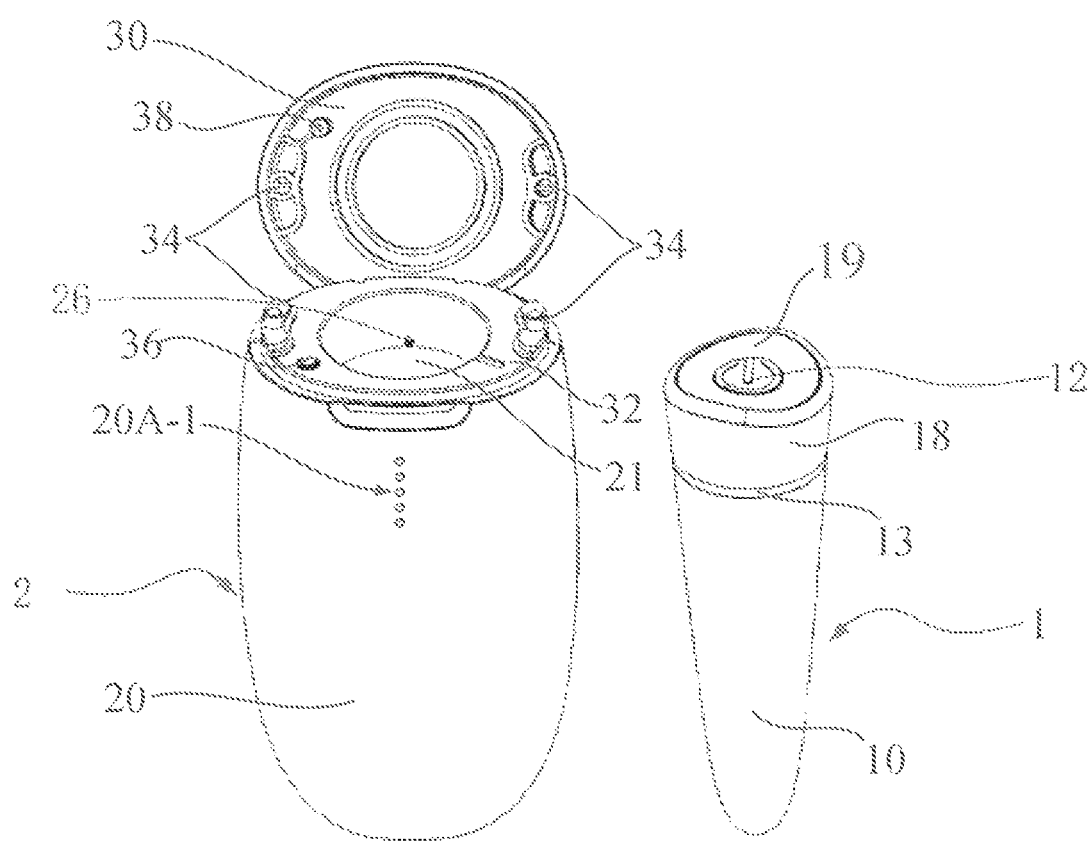
FIG. 1 is an overall structure schematic diagram showing an embodiment of the vibrating masturbator device product disclosed herein.
Figure 2:
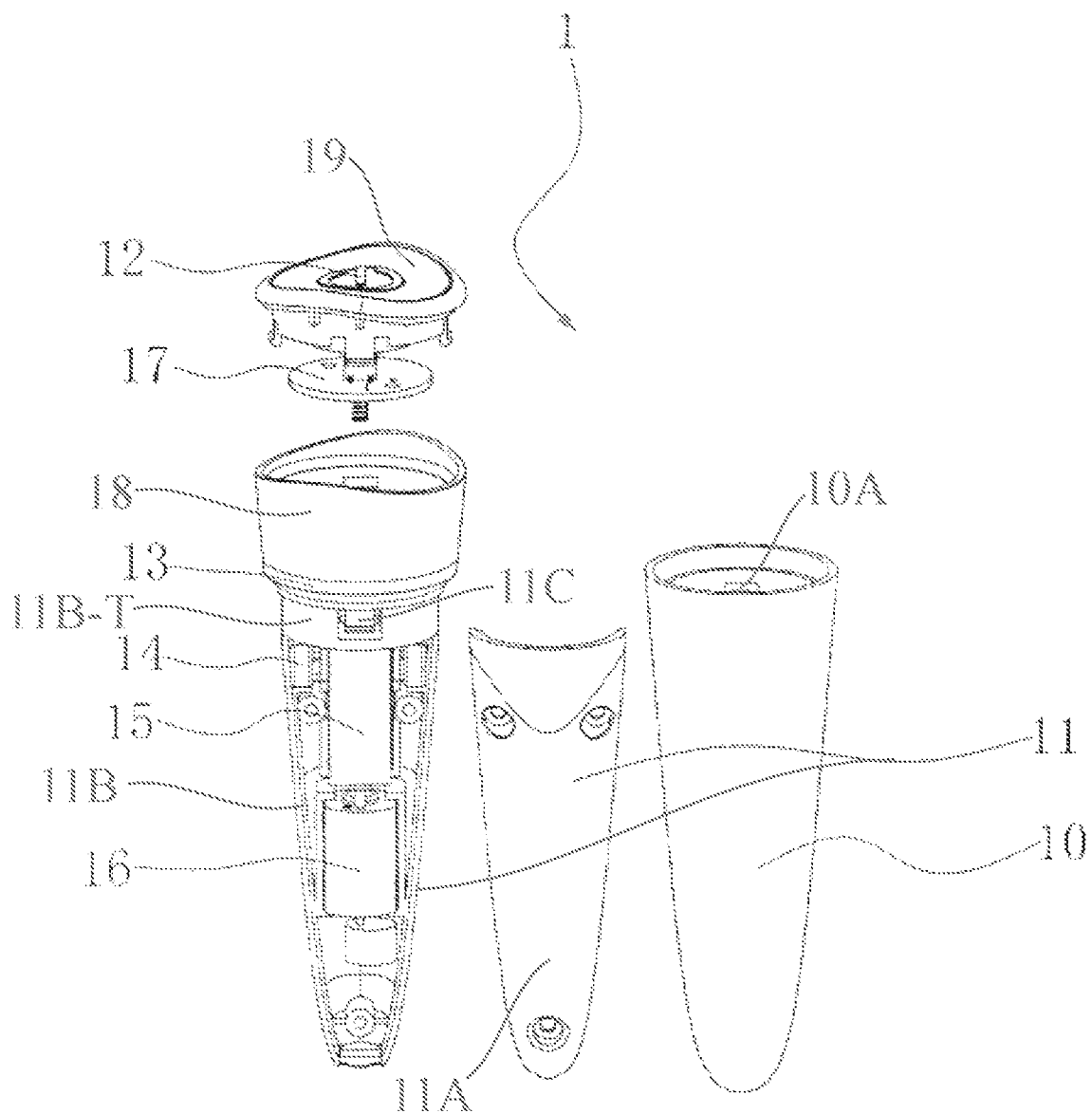
FIG. 2 is an exploded structure schematic diagram showing an embodiment of the masturbator device disclosed herein.
Figure 3:
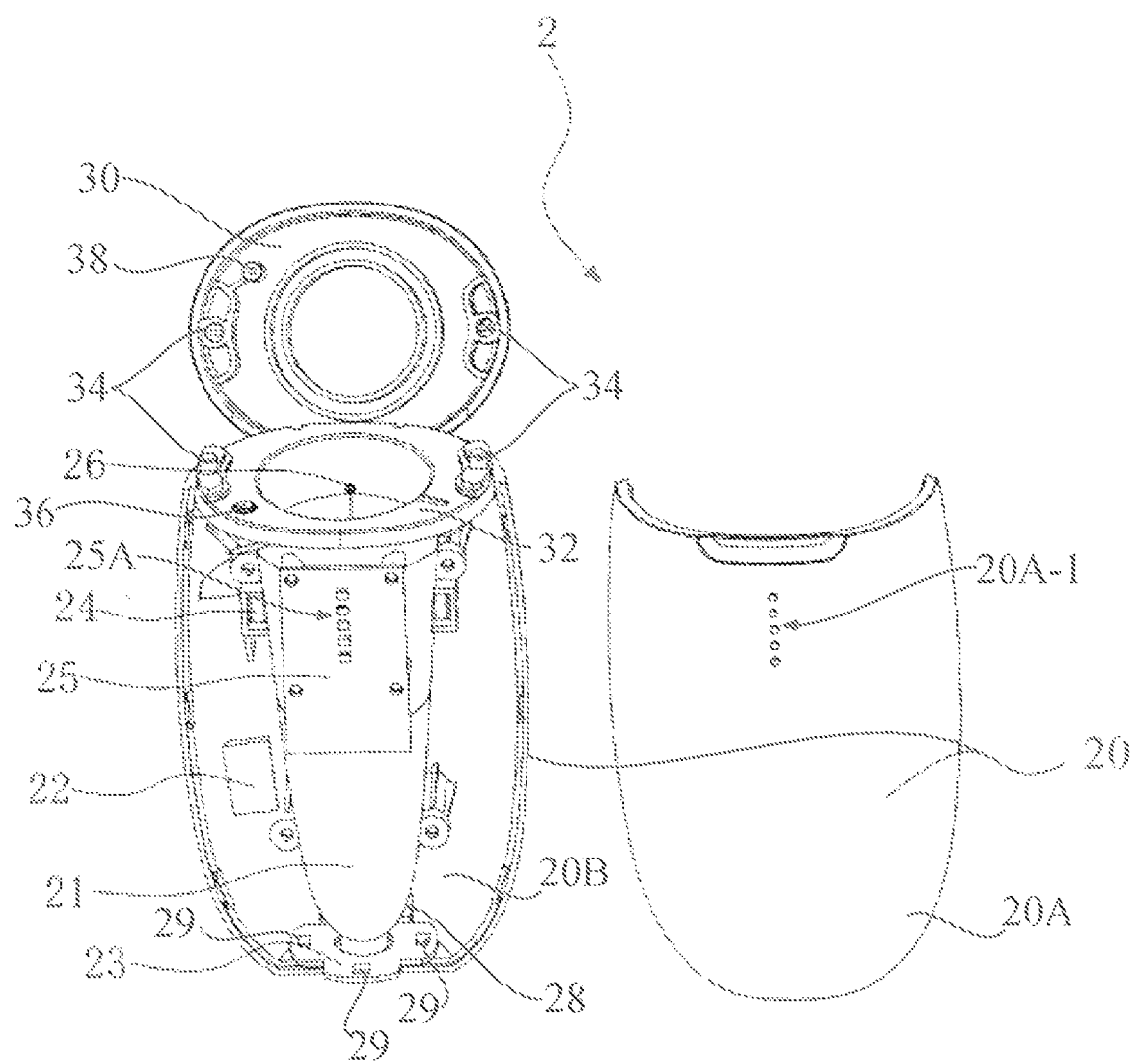
FIG. 3 is an exploded structure schematic diagram showing an embodiment of the masturbator device charging box disclosed herein.

Turning now to the Drawing Figures, which are not necessarily to scale, FIGS. 1-3 illustrate an example embodiment of a vibrating masturbator device product with sterilization and charging functions. As shown in FIG. 1, the vibrating masturbator device product according to the illustrated embodiment includes a vibrating masturbator device 1 and a charging box 2 for placing and charging the masturbator device 1.

As shown in FIG. 2, the vibrating masturbator device 1 according to the illustrated embodiment includes an outer shell 10 and a shell 11 that define a masturbator device body. The shell 11 includes a front shell half 11A and a rear shell half 11B. The outer shell 10 is connected and fixed with the shell 11 by one or more fasteners, such as a pair of front and rear spring clips 11C on the shell (only the front clip is shown) that engage front and rear spring clip retainers 10A (only the rear retainer is shown) on the outer shell.

The outer shell 10 and a lower portion of the shell 11 define a lower vibrating end of the masturbator body, and of the masturbator device 1 itself. An upper base end of the masturbator body, and of the masturbator device 1 itself, may be provided by a cowling 18 that attaches to a tubular upper end 11B-T of the rear shell half 11B. The cowling 18, which forms an upper extension of the shell 11, serves as a bezel that retains an upper end cover 19 of the masturbator device 1. The upper end cover 19, which may be transparent, forms an upper end of the shell 11. The upper end cover 19 mounts a switch control button 12.

The annular joint between the outer shell 10 and the shell 11 is provided with a ring-shaped charging sheet 13. The ring-shaped charging sheet 13 is formed as a two-piece ring having front and rear ring halves (only the front ring half is shown) that define masturbator device charging contacts. The masturbator device charging contacts are exposed laterally on the masturbator device 1, proximate to its upper base end.

The shell 11 is additionally provided with a first magnetic device 14, a masturbator device battery 15, a vibration motor 16, and a switch control plate 17. With the exception of the switch control plate 17, the foregoing components are carried by the rear shell half 11B, with the front shell half 11A serving as a removable cover. The switch control plate 17 is situated below the upper end cover 19, and is carried by the cowling 18. The first magnetic device 14 is provided on both sides of the shell 11. The masturbator device battery 15 is connected electrically to the ring-shaped charging sheet 13. The switch control button 12 is connected to the switch control plate 17, and controls the operation of the vibrator motor 16.

As shown in FIG. 3, the masturbator device charging box 2 according to the illustrated embodiment includes a charging box housing 20 and a storage compartment 21 inside the charging box housing 20. The masturbator device charging box 2 further includes a charging box battery 22, a sterilization device 23, a second magnetic device 24, and a power board 25. The charging box housing 20 includes a front housing half 20A and a rear housing half 20B. The storage compartment 21, the charging box battery 22, the sterilization device 23, the second magnetic device 24, and the power board may all be carried by the rear housing half 20B, with the front housing half 20A serving as a removable cover.

The storage compartment 21 conforms to the shape of the masturbator device body, and particularly the lateral surface contour of the outer shell 10 and the cowling 18 of the masturbator device 1. The sterilization device 23 may be located at the bottom of the storage compartment 21. Thus, the masturbator device 1 can be put into the storage compartment 21 to perform disinfection. The power board 25 includes a power indicator 25A (e.g. an array of indicator lights) located at the front of the storage compartment 21. The power indicator 25A is visible through a power indicator window 20A-1 (e.g., an array of openings) formed in the front housing half 20A. The second magnetic device 24 is fixed on both sides of the storage compartment 21 and corresponds to the position of the first magnetic device 14 on the masturbator device 1. The first magnetic device 14 in the masturbator device 1 and the second magnetic device 24 in the charging box 2 are mutually attracted. The first magnetic device 14 and the second magnetic device 24 may thus both be magnets that work through the effect of magnet attraction. The sterilization device 23 and the charging box battery 22 are electrically connected with the power board 25.

The storage compartment 21 has front and rear charging contacts 26 (only the rear contact is shown) corresponding to the position of the front and rear ring halves of the ring-shaped charging sheet 13 on the masturbator device 1. The masturbator device 1 can receive charging current through the charging contacts 26.

The masturbator device charging box 2 also has a charging port 28 for charging the battery 22 in the charging box.

The sterilization device 23 may be composed of multiple (e.g. 3-4) UVC ultraviolet disinfection lamps 29, which can provide effective sterilization of the masturbator device 1. The UVC ultraviolet disinfection lamps may be located outside (e.g., below) the charging box storage compartment 21, which may comprise UVC ultraviolet light transmissible material, in order to illuminate the masturbator device 1 with UVC ultraviolet light when it is disposed inside of the charging box storage compartment.

The masturbator device charging box 2 may be provided with a flip-open lid 30, and the upper inner end of the charging box 2 may have a protective gasket 32, which protects the masturbator device 1 from being scratched by the flip-open lid. The flip-open lid 30 may be secured in the closed position by friction latches 34. The friction latches 34 include inter-engaging friction latch components respectively formed on the inside of the flip-open lid 30 and on the upper inner end of the charging box 2. The friction latches 34 prevent inadvertent opening of the flip-open lid 30 (and emission of UVC ultraviolet light from the storage compartment 21) while the sterilization device 23 is operating. For additional safety, a switch actuator button 36 may be provided on the upper inner end of the charging box 2. The switch actuator button 36 is engaged by a switch button actuating pin 38 on the flip-open lid 30 when the lid is closed. The switch actuator button 36 actuates a switch that may be electrically connected so that the sterilization device 23 will only activate when the flip-open lid 30 is closed, and will deactivate when the flip-open lid is opened. The switch actuator button 36 may similarly be used to activate and deactivate the charging function of the masturbator device charging box 2.

Benefits of the above-described vibrating masturbator device product with sterilization and charging functions include: small size, ease of use, and portability. The masturbator device charging box 2 can support the masturbator device 1 for long-term usage with charging. In addition, the vibrating masturbator device product incorporates the sterilization device 23 inside the charging box 2, which can provide charging and disinfection at the same time when the masturbator device 1 is put into the masturbator device charging box after use, thus avoiding bodily harm the next time the masturbator device is used. Due to its battery 22, the charging box 2 is portable, and may be used to sterilize and charge the masturbator device 2 either with or without an external power source.

The above embodiments are for the purpose of illustration and not restriction of the disclosed invention. Therefore, all equivalent changes or modifications made according to the subject matter falling within the scope of the claims are included in the scope of this disclosure.

What is claimed is:

1. A vibrating masturbator device product with sterilization and charging functions, comprising:
    a masturbator device, the masturbator device comprising:
        a body;
        a switch control member on the body;
        masturbator device charging contacts exposed on the body;
        a masturbator device battery electrically connected to the masturbator device charging contacts; and
        a vibration motor powered by the battery;

a masturbator device charging box for placing and charging the masturbator device, the masturbator device charging box comprising:
a storage compartment for receiving the masturbator device;
the storage compartment conforming in shape to a vibrating end of the body of the masturbator device;
charging box charging contacts corresponding in position to the masturbator device charging contacts;
a charging box power source electrically connected to the charging box charging contacts; and
a sterilization device arranged to sterilize the masturbator device while it is being charged in the masturbator device charging box, the sterilization device being powered by the charging box power source.

2. The vibrating masturbator device product of claim 1, wherein the masturbator device body includes an outer shell and a shell, and wherein the masturbator device switch control member comprises a button located on an upper end of the shell.

3. The vibrating masturbator device product of claim 1, wherein the masturbator device charging contacts comprise a ring-shaped charging sheet.

4. The vibrating masturbator device product of claim 1, wherein the masturbator device comprises a first magnetic device on the masturbator device body, and wherein the masturbator device charging box comprises a second magnetic device on the storage compartment, the first magnetic device and the second magnetic device being arranged for mutual attraction with each other.

5. The vibrating masturbator device product of claim 1, wherein the charging box power source comprises a battery.

6. The vibrating masturbator device product of claim 1, wherein the sterilization device of the masturbator device charging box comprises an ultraviolet light source.

7. The vibrating masturbator device product of claim 1, wherein the sterilization device of the masturbator device charging box comprises UVC ultraviolet disinfection lamps.

8. The vibrating masturbator device product of claim 1, wherein the masturbator device charging box includes a housing in which the storage compartment is situated, the storage compartment being transmissible to UVC ultraviolet light, and wherein the sterilization device is outside the storage compartment in order to illuminate the masturbator device when it is inside the charging box storage compartment.

9. The vibrating masturbator device product of claim 1, wherein the masturbator device charging box comprises a flip-open lid configured to close the storage compartment when the masturbator device is received therein, and an upper inner end of the masturbator device charging box comprises a protective gasket.

10. The vibrating masturbator device of claim 9, wherein the masturbator device charging box comprises a switch actuator member that is actuated by the flip-open lid to activate the sterilization device only when the flip-open lid is closed.

11. The vibrating masturbator device of claim 1, wherein:
the masturbator device comprises:
an outer shell and a shell of the masturbator device body, and a switch control button located on an upper end of the shell that provides the switch control member;
a joint between the outer shell and the shell provided with a ring-shaped charging sheet that defines the masturbator device charging contacts;
the shell being provided with a first magnetic device, the masturbator device battery, the vibration motor, and a switch control plate; and
the first magnetic device being provided on sides of the shell, and the masturbator device battery being connected electrically to the ring-shaped charging sheet;
the masturbator device charging box comprises:
a charging box housing with the storage compartment inside the charging box housing, a charging box battery that provides the charging device power source, the sterilization device, a second magnetic device and a power board;
the sterilization device being disposed in a bottom of the storage compartment, and the power board including a power indicator located at a front of the storage compartment;
the second magnetic device being fixed on sides of the storage compartment and corresponding to a position of the first magnetic device on the masturbator device; and
the sterilization device and the charging box battery being electrically connected with the power board.

12. The vibrating masturbator device product of claim 11, wherein the masturbator device charging box includes a flip-open lid disposed at an upper end of the charging box, and wherein an upper inner end of the masturbator device charging box includes a protective gasket.

13. The vibrating masturbator device product of claim 11, wherein the sterilization device in the masturbator device charging box is composed of multiple UVC ultraviolet disinfection lamps.

14. The vibrating masturbator device product of claim 11, wherein the sterilization device in the masturbator device charging box is composed of multiple UVC ultraviolet disinfection lamps outside of the charging box storage compartment that can illuminate the masturbator device when it is inside of the charging box storage compartment.

15. The vibrating masturbator device product of claim 11, wherein the charging box storage compartment includes charging contacts corresponding to a position of the ring-shaped charging sheet on the masturbator device.

16. The vibrating masturbator device product of claim 11, wherein the first magnetic device in the masturbator device and the second magnetic device in the masturbator device charging box are mutually attracted.

17. The vibrating masturbator device product of claim 11, wherein the masturbator device charging box has a charging port for charging the charging box battery.

18. The vibrating masturbator device product of claim 11, wherein the outer shell of the masturbator device is connected and fixed with the shell of the masturbator device by a fastener.

19. A vibrating masturbator device and a masturbator device charging box for use in a vibrating masturbator device product with sterilization and charging functions;
the vibrating masturbator device comprising:
a masturbator device body having a base end and a vibrating end;
a switch control member on the masturbator device body;
masturbator device charging contacts exposed on the masturbator device body proximate to the base end of the masturbator device body;
a masturbator device battery electrically connected to the masturbator device charging contacts; and
a vibration motor powered by the battery;

the masturbator device charging box comprising:
- a storage compartment for receiving the vibrating masturbator device;
- the storage compartment having a closed end arranged to receive the masturbator device body proximate to its vibrating end and an open end arranged to receive the masturbator device body proximate to its base end, the open end defining an entrance through which the vibrating masturbator device is inserted in order to be received in the storage compartment;
- charging box charging contacts proximate to the open end of the storage compartment and positioned to engage the masturbator device charging contacts when the vibrating masturbator device is received in the storage compartment;
- a charging box power source electrically connected to the charging box charging contacts; and
- a sterilization device arranged to sterilize the vibrating masturbator device while it is being charged in the masturbator device charging box, the sterilization device being powered by the charging box power source.

20. A masturbator device charging box for use in a vibrating masturbator device product with sterilization and charging functions, the masturbator device charging box comprising:
- a storage compartment for receiving a vibrating masturbator device;
- charging contacts corresponding in position to charging contacts on the masturbator device;
- a charging box power source electrically connected to the charging box charging contacts;
- a light-emitting sterilization device arranged to sterilize the masturbator device while it is being charged in the masturbator device charging box, the sterilization device being powered by the charging box power source;
- a housing in which the storage compartment is situated, the storage compartment being transmissible to light emitted by the sterilization device; and
- the sterilization device being outside the storage compartment in order to illuminate the vibrating masturbator device when it is inside the box storage compartment.

* * * * *